United States Patent [19]
Ho et al.

[11] Patent Number: 5,326,920
[45] Date of Patent: Jul. 5, 1994

[54] ISOBUTYLENE OLIGOMERIZATION USING SUPPORTED ACID CATALYSTS

[75] Inventors: Suzzy C. Ho, Plainsboro; Margaret M. Wu, Skillman, both of N.J.

[73] Assignee: Mobil Oil Corporation, Fairfax, Va.

[21] Appl. No.: 57,030

[22] Filed: May 5, 1993

Related U.S. Application Data

[63] Continuation-in-part of Ser. No. 996,385, Dec. 22, 1992, Pat. No. 5,294,578.

[51] Int. Cl.$^5$ ................................ C07C 2/00
[52] U.S. Cl. ................... 585/528; 585/520; 585/527; 585/530; 585/532; 585/533
[58] Field of Search ............. 585/520, 527, 528, 530, 585/532, 533

[56] References Cited

U.S. PATENT DOCUMENTS

| | | | |
|---|---|---|---|
| 2,397,945 | 4/1946 | Burney et al. | 585/532 |
| 3,248,343 | 4/1966 | Kelly et al. | |
| 3,629,150 | 12/1971 | Addy | 585/533 |
| 4,048,108 | 9/1977 | Ryu | 585/533 |
| 4,152,499 | 5/1979 | Boerzel et al. | 526/52.4 |
| 4,517,075 | 5/1985 | Dessau et al. | 585/533 |
| 4,605,808 | 8/1986 | Samson | 585/525 |
| 4,719,190 | 1/1988 | Drago et al. | 502/64 |
| 4,740,652 | 4/1988 | Frame | 585/512 |
| 4,849,572 | 7/1989 | Chen et al. | 585/525 |
| 4,929,800 | 5/1990 | Drago et al. | 585/533 |
| 5,012,030 | 4/1991 | Lane et al. | 585/527 |
| 5,068,490 | 11/1991 | Eaton | 585/525 |

FOREIGN PATENT DOCUMENTS 225423 7/1985 German Democratic Rep.

OTHER PUBLICATIONS

Inorganic Chemistry, vol. 29, No. 6, 1990, pp. 1186–1192 Krzywicki et al., "Superacidity of Modified Gamma-Al$_2$O$_3$", Faraday I, 1980, 76, 1311–1322.

Primary Examiner—Patrick P. Garvin
Assistant Examiner—E. D. Irzinski
Attorney, Agent, or Firm—Alexander J. McKillop; Dennis P. Santini; Laurence P. Hobbes

[57] ABSTRACT

A process for the production of polyisobutylene (PIB) from isobutene-containing feed comprises contacting said feed with a catalyst composition comprising halides of a metal component anchored on an adsorbent inorganic oxide solid by an oxygen-metal bond to provide a reaction mixture containing said polyisobutylene; and thereafter separating and recovering said polyisobutylene.

19 Claims, 2 Drawing Sheets

ISOBUTYLENE OLIGOMERIZATION USING SUPPORTED ACID CATALYSTS

REFERENCE TO COPENDING APPLICATIONS

This application is a continuation-in-part of U.S. patent application Ser. No. 07/996,385, filed Dec. 22, 1992 now U.S. Pat. No. 5,294,578 and is related in subject matter to U.S. patent application Ser. No. 08/057,029, filed contemporaneously herewith.

BACKGROUND OF THE INVENTION

1. Field of the Invention

This invention relates to supported acid catalysts, their method of preparation and use in hydrocarbon conversion reactions, specifically isobutylene oligomerization reactions. The catalyst composition contains metal halides on a solid inorganic oxide support. The composition is prepared by reacting an adsorbent solid support containing surface hydroxide groups with organic metal halide wherein said metal is a single element selected from one of Groups IIA, IIB, IIIA, IIIB, IVB, VB, and VIB e.g., Al, under conditions sufficient for the organic metal halide to react with at least a portion of the surface hydroxyl groups.

2. Prior Art

Conventional Friedel-Crafts catalysts, e.g., $AlCl_3$ and $BF_3$, have been used extensively in many industrial processes as well as in the laboratory. The major drawback of these systems is the need to dispose of large volumes of liquid and gaseous effluents produced during subsequent quenching and product washing. Replacing these processes by those based on heterogeneous catalysis has environmental and economic advantages, e.g., ease of separation, catalyst recycling and elimination of quenching and washing steps.

The literature discloses efforts to anchor $AlCl_3$ onto a solid support. Alumina can be chlorided with $AlCl_3$, HCl, or $Cl_2$. U.S. Pat. No. 3,248,343 to Kelly et al. teaches the treatment of surface hydroxyl-containing supports, e.g., alumina or silica gel, with aluminum halide and thereafter treating with hydrogen halide. Refluxing $AlCl_3$ with solid supports, e g., silica, in chlorinated solvent, e.g., $CCl_4$, is an alternate way of anchoring Lewis acid onto a support as disclosed in U.S. Pat. No. 4,719,190 to Drago et al and Getty et al., "Preparation, Characterization, and Catalytic Activity of a New Solid Acid Catalyst System," *Inorganic Chemistry*, Vol. 29, No 6, 1990, 1186–1192. However, these methods suffer from incomplete reaction between $AlCl_3$, HCl or $Cl_2$ and the support, resulting in catalyst that either contains a low concentration of the acidic species or is not very stable due to the leachability of physisorbed or chemisorbed $AlCl_3$ species from the solid support. Krzywickl et al., "Superacidity of Modified Gamma-$Al_2O_3$,"J. C. S. Faraday I, 1980, 76, 1311-1322 teach the treatment of alumina with a metal-alkyl species, e.g., $CH_3AlCl_2$ vapors, to prepare a superacid catalyst which can catalyze the transformation of saturated hydrocarbons. U.S. Pat. No. 4,740,652 to Frame discloses an olefin oligomerization catalyst which comprises a porous support, e.g., silica, and plural metal components, an iron group metal, e.g., Ni, and alkyl aluminum compound, e.g., diethylaluminum chloride and aluminum halide, e.g., aluminum trichloride Such catalysts are used in transition metal catalyzed chemistry.

East German Patent DD225423 to Hallpap, et al. discloses a catalyst comprising alkyl aluminum halide supported on a silica support which is used for converting C4 isobutene-containing feeds to polyisobutylenes (PIBs). The catalyst is prepared from silica dried at 190° C., and no initiator for cationic isobutene oligomerization is used.

BRIEF SUMMARY OF THE INVENTION

The present invention relates to a process for the production of polyisobutylene (PIB) from isobutene which comprises:

contacting isobutene-containing feed, under heterogeneous oligomerization conditions with a catalyst composition comprising halides of a metal component anchored on an adsorbent inorganic oxide solid by an oxygen-metal bond and a promoter selected from the group consisting of water, alkanol, alkyl halide and HCl, to provide a reaction mixture containing said polyisobutene, wherein said inorganic oxide support is heated at temperatures ranging from 300° to 600° C., prior to said contacting of the support;

and separating and recovering said polyisobutene.

In a more particular aspect, the present invention relates to a process wherein the metal is a single element selected from one of Groups IIA, IIB, IIIA, IIIB, IVB, VB and VIB, and the adsorbent inorganic oxide is selected from the group consisting of silica silica-alumina, clay, crystalline porous silicates, silicoaluminophosphates, titania, vanadia, and rare earth oxides The contacting can be carried out in the presence of a promoter selected from the group consisting of water, alkanol, e.g., methanol, alkyl halide and HCl The promoter acts as a proton source to effect cationic mechanism of reaction.

The present invention further relates to a method of isobutene oligomerization which employs a catalyst composition consisting essentially of halides of a single metal component anchored on an adsorbent solid by an oxygen-metal bond. The catalyst can be prepared by a method which utilizes an adsorbent inorganic oxide support containing surface hydroxyl groups which has been dried at a temperature of 300° to 600° C. The high temperature drying process is necessary to remove excess surface hydroxyls in order to form isolated surface hydroxyl groups. Reactions of the isolated hydroxyl groups with organic metal halides (Reaction I) result in the anchoring of the metals through the formation of single metal-oxygen bond. Without high temperature dehydration adjacent surface hydroxyls can react with organic metal halides (reaction II) to anchor the metals through two metal-oxygen bonds Metal centers containing two oxygen ligands are less Lewis acidic and therefore less active in cationic reaction than those with one oxygen ligand.

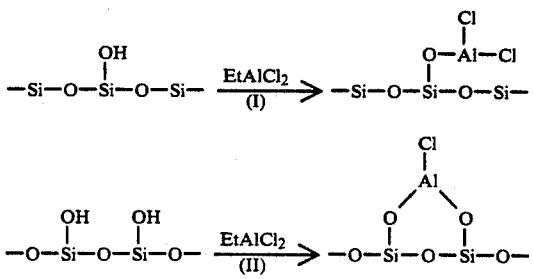

The high temperature treated support is contacted with organic metal halide, under conditions sufficient for the organic metal halide to react with at least a portion of the surface hydroxyl groups. The metal can be a single element selected from one of Groups IIA, IIB, IIIA, IIIB, IVB, VB, and VIB, and the adsorbent inorganic oxide support is selected from the group consisting of silica, silica-alumina, clay, crystalline porous silicates, silicoaluminophosphates, titania, vanadia, and rare earth oxides. Reaction between the organic metal halide and the surface hydroxyl group can proceed readily at moderate conditions, e.g., room temperature and atmospheric pressure, eliminating the organic ligand and forming a metal-oxygen bond. Preferably such reaction is carried out in the presence of a relatively inert hydrocarbon liquid solvent, such as alkanes, e.g., n-hexane, rather than a more active material such as olefin in order to prevent olefin oligomerization reactions catalyzed by the organic metal halides and the surface hydroxyls as promoters (Reaction III).

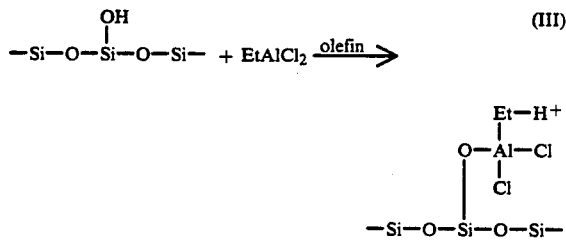

Aluminum alkyl halide reacts with surface hydroxyl groups of a silanol-containing support as follows:

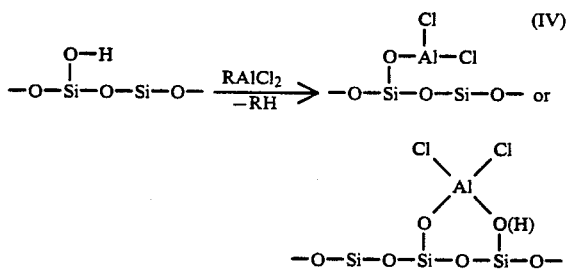

The catalyst compositions thus prepared comprise Lewis acidic catalysts, e.g., $AlCl_3$, $BF_3$, and $GaCl_3$, anchored on the support surface by formation of an oxygen-metal bond. The resulting solid catalysts containing these metals will catalyze hydrocarbon conversion reactions such as olefin oligomerization reactions.

In another aspect, the invention relates to the use in isobutene oligomerization of a solid acid catalyst composition which consists essentially of halides of at least one major group element (non-transition elements) on an inorganic oxide adsorbent solid support containing surface silanol groups. Such major group metals included Lewis acidic metals such as Al, B and Ga. Such a composition is prepared by reacting an adsorbent solid support containing surface silanol groups with organic metal halide wherein said metal is one or more major group elements, e.g., Lewis acidic metals (e.g., Al, B, and Ga), under conditions sufficient for the organic metal halide to react with at least a portion of the surface hydroxyl groups.

DETAILED DESCRIPTION OF THE INVENTION

Figure 1:
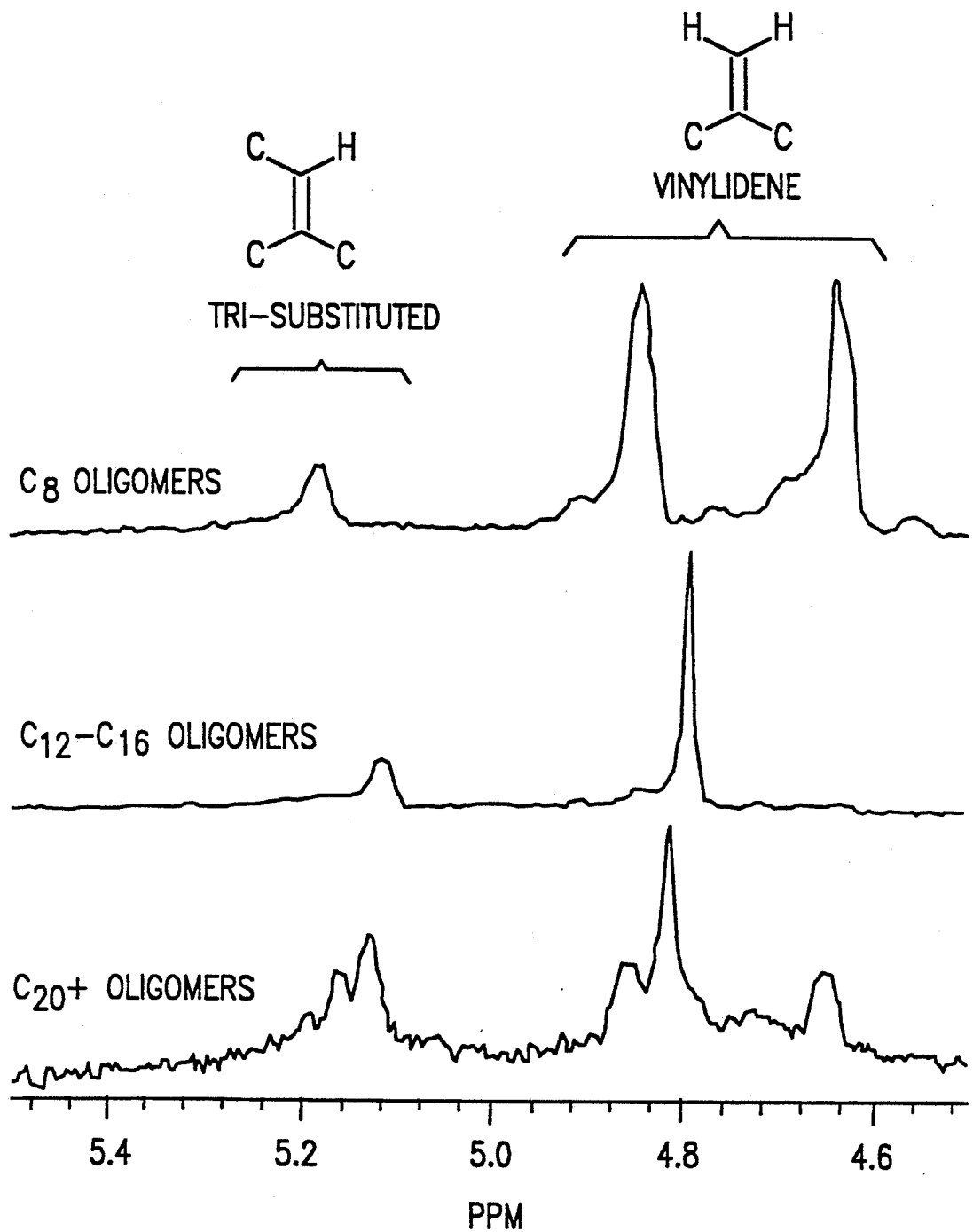
FIG. 1 is a graph comparing the H-1 NMR spectra of ! isobutylene oligomers in the vinyl region and PIBs prepared in accordance with the present invention

The inorganic porous support materials useful in the present invention are typically inorganic oxides of silica, silica-alumina, silica-thoria, silica-zirconia, clays, crystalline silicates, e.g., zeolites, and silicoaluminophosphates (SAPOs) and comparable oxides which are porous, and have surface hydroxyl groups, viz., silanol groups. Other suitable inorganic porous support materials include titania, zirconia, alumina, vanadia, and rare-earth oxides which. have surface hydroxyl groups.

Preferred silica support materials are amorphous silica, silica gels or xerogels with high porosity, preferably having pores of at least 10 Angstroms, more preferably at least 20 Angstroms, e.g., 20 to 460 Angstroms or 60 to 250 Angstroms. suitable particle sizes for such silica supports range from 1 to 600 mesh, preferably 30 to 400 mesh, e.g., 30 to 60 or 90 to 300 mesh size. The solid support materials can be calcined, preferably under an inert gas, e.g., nitrogen, at a suitable temperature for a sufficient time to remove physically-bound water and/or to partially remove chemically-bound water. Such temperatures can range from about 100° to 900° C., preferably 300 to 600° C., and contacting times can range from 0.1 to 24 hours, preferably 1 to 8 hours. The extent of loading of the halides a single metal component on the hydroxyl-containing support can be increased by moderating the calcination carried out upon the support prior to contact with the organic metal halide, e.g, reducing calcination temperatures from about 600° C. to 300° C. This is especially effective with silica gel supports. Generally, after treatment with organic metal halide, the metal halides are present in the amount of 0.01 to 10 mmole/g of the catalyst composition.

Naturally occurring clays which can be used as supports herein include the montmorillonite and kaolin families which include the subbentonites, and the kaolins commonly known as Dixie, McNamee, Georgia and Florida clays, or others in which the main mineral constituent is halloysite kaolinite, dickite, nacrite or anauxite. Such clays can be used in the raw state as originally mined or initially subjected to calcination acid treatment or chemical modification.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as rigid three-dimensional frameworks of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, St/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolites have come to be designated by letter or other convenient symbols as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983 ), zeolite ZSM-35 (U.S. Pat. No. 4,016,245), zeolite ZSM-38 (U.S. Pat. No. 4,046,859), zeolite ZSM-23 (U.S. Pat. No. 4,076,842) and MCM-22 (U.S. Pat. No. 4,954,325) merely to name a few.

Silicoaluminophosphates of various structures are taught in U.S. Pat. No. 4,440,871 include SAPO-5, SAPO-11, SAPO-16, SAPO-17, SAPO-20, SAPO-31, SAPO-34, SAPO-35, SAPO-37, SAPO-40, SAPO-41, SAPO-42, and SAPO-44. Other teachings of silicoaluminophosphates and their synthesis include U.S. Pat. No. 4,673,559 (two-phase synthesis method); U.S. Pat. No. 4,623,527 (MCM-10); U.S. Pat. No. 4,639,358 (MCM-1); U.S. Pat. No. 4,647,442 (MCM-2); U.S. Pat. No. 4,664,897 (MCM-4); U.S. Pat. No. 4,639,357 (MCM-5); U.S. Pat. No. 4,632,811 (MCM-3); and U.S. Pat. No. 4,880,611 (MCM-9).

Mesoporous siliceous materials are recent developments in catalyst technology having novel pore geometry which are suitable as molecular sieves having openings of at least 8 Angstroms which are used as components of the layered catalyst of the present invention. Such materials can be described as inorganic, porous non-layered crystalline phase material exhibiting after calcination, an X-ray diffraction pattern with at least one peak at a d-spacing greater than about 18 Angstrom Units and having a benzene adsorption capacity of greater than 15 grams benzene per 100 grams of said calcined material at 50 tort and 25° C. Such materials can further be characterized by substantially uniform hexagonal honeycomb microstructure, with uniform pores having a cell diameter greater than 13 Angstrom units, say, 15 Angstrom Units (preferably in the mesoporous range of about 20-100A). Most prominent among these ultra-large pore size materials is a class of materials known as M41S which are described further in U.S. Pat. No. 5,102,643, including a metallosilicate called MCM-41, which is usually synthesized with Bronsted acid active sites by incorporating a tetrahedrally coordinated trivalent element, such as Al, Ga, B, or Fe, within the silicate framework. Aluminosilicate materials of this type are thermally and chemically stable, properties favored for acid catalysis; however, the advantages of mesoporous structures may be utilized by employing highly siliceous materials or crystalline metallosilicate having one or more tetrahedral species having varying degrees of acidity. In addition to the preferred aluminosilicates, the gallosilicate, ferrosilicate and borosilicate materials may be employed Although matrices may be formed with the germanium analog of silicon, these are expensive and generally no better than the metallosilicates.

MCM-41 crystalline structure is readily recognized by its spectrographic characteristics, such as electron micrograph, X-ray diffraction pattern, absorption properties, etc., as described in U.S. Pat. No. No 5,098,684.

All of the above patents are incorporated herein by reference.

The organic metal halide employed in the present invention can comprise one or more metal elements selected from Groups IIA, IIB, IIIA, IIIB, IVB, VB, and VIB of the Periodic Table, under conditions sufficient for the organic metal halide to react with at least a portion of the surface hydroxyl groups. Suitable organic metal halides include those represented by the formula RMXY wherein R is alkyl, alkenyl, or aryl, M is an element selected from Groups IIA, IIB, IIIA, IIIB, IVB, VB, and VIB of the Periodic Table, X is halogen and Y is selected from the group consisting of halogen, alkyl, alkenyl, aryl, alkoxy, and amido moities. In one embodiment, R is alkyl, M is a Group IIIA element, e.g., Al, B, or Ga, and Y is selected from the group consisting of halogen, e.g., Cl or Br, and alkyl. A particularly preferred organic metal halide is one wherein RMXY is selected from the group consisting of $EtAlCl_2$, $Me_2AlCl$, $Et_2AlCl$, $Et_2AlCl$ $EtAlCl_2$, and $Et_2AlOMe$, with $EtAlCl_2$ particularly preferred.

Generally, the support is combined with a suitable solvent in amounts sufficient to form a slurry. The slurry is then combined with the organic metal halide which can also be combined with a suitable solvent in order to facilitate handling and mixing. Such solvents are preferably inert to reaction with the support and organic metal halide. Examples of suitable solvents include alkanes which are liquid under standard conditions such $C_4$ to $C_{16}$ alkanes, e.g., n-pentane, n-hexane, or n-heptane.

The conditions used to prepare the catalysts of the present invention are those which allow the organic metal halide to react with at least a portion of the surface hydroxyl groups on the adsorbent solid support. Suitable conditions for contacting the support with organic metal halide comprise temperatures of $-78°$ to 120° C., pressures of $10^{-6}$ atm to 10 atm, and reaction time of 0.01 to 10 hours. Preferred conditions include temperatures of 20° to 60° C., pressures of $10^{-1}$ to 1 atm, and reaction time of 0.5 to 2 hours. It is preferred that the catalysts of the present invention be prepared under an inert atmosphere, e.g., nitrogen or helium, in order to prevent unwanted hydrolysis of the organic metal halides. Such conditions can be obtained using conventional Schlenk line techniques Following the reaction the catalyst may be separated from the reaction mixture according to any conventional procedure for removing solids from the liquid solvent medium, e.g., decantation or filtration. The catalyst is ready for use after the drying step as described below. In another method of preparation, the resulting solid can be washed with a suitable liquid, e.g. inert organics, e.g., anhydrous $C_4$ to $C_6$ alkanes, e.g., n-hexane. Such washing is preferably carried out a sufficient number of times to substantially remove excess organic metal halides. The washed catalyst is then dried, preferably under vacuum, at temperatures ranging from 0° to 120° C., preferably 20° to 60° C. The dried catalyst is then stored under inert atmosphere, e.g., in a nitrogen filled box.

The amount of metal halides or organo-metal halides deposited onto the solid can range from 0.01 mmole to 10 mmoles of metal halides or organometal halides per g of catalyst. Generally, the lower calcination temperature for the solid, the more organometal halide one can deposit onto the solid.

The catalyst thus prepared is suited to use in the catalytic conversion of organic, e.g., hydrocarbon feeds. In general, catalytic conversion conditions over the present catalyst include a temperature of from about $-100°$ C. to about 760° C., a pressure of from about 0.1 atmosphere (bar) to about 200 atmospheres (bar), a weight hourly space velocity of from 0.08 to 2000 $hr^{-1}$ and a hydrogen/organic, e.g., hydrocarbon, compound ratio of from 0 to 100.

Non-limiting examples of such conversion processes include: cracking hydrocarbons with reaction conditions including a temperature of 300° to 700° C., a pressure of 0.1 to 30 atmospheres (bar) and a weight hourly space velocity of from 0.1 to 20 $hr^{-1}$; dehydrogenating hydrocarbon compounds with reaction conditions including a temperature of 300° to 700° C., a pressure of 0.1 to 10 atmospheres (bar) and a weight hourly space velocity of from 0.1 to 20 $hr^{-1}$ converting paraffins to aromatics with reaction conditions including a temperature of 100° to 700° C., a pressure of 0.1 to 60 atmospheres (bar) and a weight hourly space velocity of from 0.5 to 400 $hr^{-1}$ and a hydrogen/hydrocarbon ration of from 0 to 20; converting olefins to aromatics, e.g., benzene, toluene and xylenes, with reaction conditions including a temperature of 100° to 700° C., a pressure of 0.1 to 60 atmospheres (bar) and a weight hourly space velocity of from 0.5 to 400 hr 1 and a hydrogen/hydrocarbon ratio of from 0 to 20; converting alcohols, e.g., methanol, or ethers, e.g., dimethylether, or mixtures thereof, to hydrocarbons including aromatics with reaction conditions including a temperature of 275° to 600° C., a pressure of 0.5 to 50 atmospheres (bar) and a weight hourly space velocity of from 0.5 to 100 $hr^{-1}$; isomerizing xylene feedstock components with reaction conditions including a temperature of 230° to 510° C., a pressure of 3 to 35 atmospheres (bar), a weight hourly space velocity of from 0.1 to 200 $hr^{-1}$, and a hydrogen/hydrocarbon ratio of from 0 to 100; disproportionating toluene with reaction conditions including a temperature of 200° to 760° C., a pressure of atmospheric to 60 atmospheres (bar) and a weight hourly space velocity of from 0.08 to 20 $hr^{-1}$.

The catalysts of the present invention are particularly useful in processes which rely on a cationic mechanism, e.g., acidic catalysis reactions. All these reactions can be carried out in a fixed-bed, continuous flow reactor or in a slurry, batch-type operation or continuous stirred tank reactor (CSTR) type operation.

Batch-type operations can be carried out by bubbling isobutylene gas through a slurry of catalyst in hydrocarbon solvent. Olefin conversion can be improved by using a mass flow meter to regulate the rate of isobutylene feed. Alternatively, isobutylene can be liquified under pressure and fed using an ISCO pump to a pressurized reactor.

Olefin oligomerization or polymerization reactions of the present invention can be carried out under reaction conditions including a temperature of $-100°$ to 300° C., preferably $-50°$ to 200° C., a pressure of $10^{-6}$ to 60 atmospheres (bar) preferably 0.1 to 10 atmospheres (bar) and a weight hourly space velocity of from 0.1 to 400, preferably 0.1 to 20.

The catalysts of the present invention are particularly suited to use in oligomerization of isobutene to produce polylsobutylene. Polyisobutylene (PIB) is an essential component used in the synthesis of gasoline and lubricant additives which is manufactured commercially by the oligomerization of isobutene in continuous-flow processes using aluminum chloride or boron trifluoride as catalysts. The products from these commercial processes can have high halide contents which interfere with their subsequent functionalization in the synthesis of additives PIBs are often reacted with maleic anhydrides to form adducts known as polyisobutenyl succinic anhydride (PIBSA) which are valuable products forming the basis of many lubricating oil additives. The polyisobutenyl-substituted saturated aliphatic anhydrides can be used per se, or as intermediates in the synthesis of diester amide, imide, amidine, and imidine addition agents in petroleum products. Such addition agents when derived from polyisobutenes of 500 to 5000 number average molecular weight have found extensive use as detergent-dispersants in motor oils and lesser use as carburetor detergents in gasoline, heat exchanger antifoulants in refinery streams, rust and corrosion inhibitors in surface coatings, and as emulsifiers and demulsifiers.

The unsaturation used for further functionalization in the commercially available PIBs is usually a tri-substituted double bond, the thermodynamic product, which is less reactive than the kinetically derived vinylidene double bond PIBs which have terminal unsaturation. Efforts have been made to increase vinylidene double bond content and are disclosed in U.S. Pat. Nos. 4,152,499, 4,605,808, 4,849,572, 5,012,030 and 5,068,490, all of which are incorporated herein by reference. Currently, PIBs are manufactured by cationic oligomerization processes using either boron trifluoride or aluminum trichloride as catalysts in homogeneous reactions. Such techniques usually require quenching of the reaction and washing with water. With an increase of environmental restrictions on the chemical industries, there is a need to eliminate the waste streams generated by these homogeneous processes by the use of catalyst recycling and the disposal of aqueous waste generated from the quenching and washing steps.

An alternative to such additional steps is to use heterogeneous catalyst which has the potential of reducing both aqueous and solid wastes. A solid catalyst can be separated from the liquid products by filtration and thus eliminates the aqueous catalyst quenching and product washing steps which tend to leave residual halides in the products, which can result in greater hydrofinishing catalyst consumption. The use of heterogeneous catalyst is of special utility in preparing lubricant compositions of low halide content, say less than 100 ppm Cl, preferably less than 40 ppm Cl.

Oligomerization conditions especially suited for oligomerization of isobutene to form PIBs comprise temperatures of −100° to 300° C., preferably 0° to 75° C., contacting times of 0.01 to 100 h, preferably 0.1 to 20 h, olefin conversion of at least 70 wt % preferably 80 to 95 wt %, $C_{20}+$ selectivity of at least 15% preferably at least 60% and said polyisobutylene has a halogen content of <100 ppm, preferably <40 ppm, weight average molecular weight ($M_w$) of 280 to 200,000 preferably 280 to 20,000, number average molecular weight ($M_n$) of 280 to 10,000, preferably 280 to 2000, molecular weight distribution of at least 1.01, preferably 11 to 20, and at least 30 wt % preferably at least 50 wt % vinylidene-type double bond content.

Suitable isobutene-containing feeds include mixtures of isobutene, 1-butene, cis and trans-2-butene, and/or isobutane obtained from refinery feedstocks and effluents. In one preferred embodiment, an isobutene feed can be purified by passing over a reduced copper catalyst such as catalyst R3-11, available from Chemical Dynamics, Corp., S. Plainfield, N.J., alumina and 4A molecular sieve before use.

For oligomerization according to the present invention, the adsorbent component from which the catalyst is prepared can have a pore size of 20 to 400 angstroms, preferably 40 to 400 angstroms, and a particle size of 1 to 400 mesh, preferably 35 to 400 mesh.

In order to more fully illustrate the nature of the invention and the manner of practicing same, the following examples are presented. It will be understood that the examples are illustrative only and that various modifications may be made in the specified parameters without departing from the scope of the invention.

EXAMPLE 1

In a 100 mL Schlenk flask was placed 10 g of 20A silica gel (calcined at 600° C. under nitrogen for 15 hours and stored under nitrogen atmosphere) and 40 mL of anhydrous hexane. 5 g of 25 wt % solution of $EtAlCl_2$ in hexane was added to the slurry via syringe. During the addition-step a stoichiometric amount of ethane evolution was observed. The mixture was stirred at room temperature for one hour. The supernatant was removed and the solids were washed with 20 mL of anhydrous hexane three times. The solids were dried under vacuum at room temperature or 50° C. for one hour.

EXAMPLES 2 to 12

The method in Example 1 was used with different silica and reagents as indicated in Table 1.

TABLE 1

| | Catalyst Preparation | | | |
|---|---|---|---|---|
| EXAMPLE | SUPPORT | TEMP* | REAGENT | (mmol:g) |
| 1 | 20A silica | 600° C. | $EtAlCl_2$ | <<1.0:1** |
| 2 | 40A silica | 600° C. | $EtAlCl_2$ | 1.0:1 |
| 3 | 60A silica | 600° C. | $EtAlCl_2$ | 1.0:1 |
| 4 | 150A silica | 600° C. | $EtAlCl_2$ | 1.0:1 |
| 5 | 60A silica | 300° C. | $EtAlCl_2$ | 1.0:1 |
| 6 | 60A silica | 300° C. | $EtAlCl_2$ | 2.0:1 |
| 7 | 60A silica | 600° C. | $EtAlCl_2$ | 2.0:1 |
| 8 | 60A silica | 600° C. | $Me_2AlCl$ | 1.0:1 |
| 9 | 60A silica | 600° C. | $Et_2AlCl$ | 1.0:1 |
| 10 | 60A silica | 600° C. | $Et_2AlCl/$ $EtAlCl_2$ | 1.0:1 |
| 11 | 60A silica | 600° C. | $Et_2AlOMe$ | 1.0:1 |
| 12 | 50A MCM-41 | 538° C. | $EtAlCl_2$ | 1.0:1 |

TABLE 1-continued

| | Catalyst Preparation | | | |
|---|---|---|---|---|
| EXAMPLE | SUPPORT | TEMP* | REAGENT | (mmol:g) |
| 13 | gamma $Al_2O_3$ | 600° C. | $EtAlCl_2$ | 1.0:1 |

*By titration, $SiO_2$ calcined at 300° C. contains 3.0 mmol of Si—OH/g of $SiO_2$
By titration, $SiO_2$ calcined at 600° C. contains 2.1 mmol of Si—OH/g of $SiO_2$
**Reaction between Si—OH and $EtAlCl_2$ was minimal as indicated by the removal of $EtAlCl_2$ during subsequent hexane wash.

EXAMPLES A to I

Preparation of $SiO_2/AlCl_2$

Isobutene Oligomerization Catalysts

Catalyst I—A 35–60 mesh 60A silica gel was calcined at 600° C. for 15hours. To a slurry of 99.5 g of this silica in anhydrous hexane was added a solution of 100 mmol of $EtAlCl_2$ in hexane. The resulting slurry was stirred at room temperature for one hour and the supernatant was decanted and the solid was dried under vacuum at 50° C. for 2 hours. A dried solid weighing 113 g was obtained and stored in a nitrogen filled box before use Catalyst II—The same procedure was used to prepare a second isobutene oligomerization catalyst except that a 100–200 mesh 150A silica was used in place of the 35–60 mesh 60A silica gel.

Chemical grade isobutene, obtained from Matheson of East Rutherford, N.J. was dried over copper chromite, alumina and 4 A molecular sieves. Methanol obtained from J. T. Baker Co. of Phillipsburg, N.J. and t-butyl chloride obtained from Aldrich were used without purification Catalysts were loaded into fixed bed or Parr reactors in a nitrogen filled box. The molecular weights of the $C_{20}+$ fractions were measured by gel permeation chromatography using polystryrenes as standards.

a) Fixed Bed Reactor

To a ⅜ reactor were loaded five grams of the $SiO_2$—$AlCl_2$ (Catalyst I) in a nitrogen filled box. A solution of 182 microliters of methanol in heptane as cationic initiator was passed through the reactor first followed by the introduction of isobutene. No isobutene purification procedure was employed Products were vacuum distilled to remove $C_{20}-$ components.

Because the fixed bed unit did not contain a cooling mechanism only reaction temperatures above 30° C. were screened due to the exothermic nature of the olefin oligomerization reaction. At 1 WHSV, olefin conversions were greater than 95% from reaction temperature of 30° to 100° C. Higher reaction temperature resulted in lower molecular weight products as indicated by the weight decrease of $C_{20}+$ fractions. Further results are set out in Table 2 below.

TABLE 2

| Fixed Bed Reactor with 5 g of Catalyst I (4.5 mmol $AlCl_2$) and 182 microliters, 4.8 mmol MeOH | | | | |
|---|---|---|---|---|
| | A | B | C | D |
| Temperature, °C. | 31 | 50 | 75 | 100 |
| WHSV | 0.94 | 0.94 | 0.94 | 0.94 |
| Time on Stream, h | 20 | 24 | 24 | 26 |
| Conversion, % | >95 | >95 | >95 | >95 |
| % $C_{20}+$ Selectivity | 40.1 | 28.1 | 18.1 | — |
| $M_n$* | 559 | 393 | 250 | — |
| $M_w$* | 5414 | 2095 | 275 | — |

TABLE 2-continued

Fixed Bed Reactor with 5 g of Catalyst I (4.5 mmol AlCl$_2$)
and 182 microliters, 4.8 mmol MeOH

| | A | B | C | D |
|---|---|---|---|---|
| MWD* | 9.7 | 5.3 | 1.1 | — |

*M$_n$ - Number Average MW of C$_{20}^+$ product
*M$_w$ - Weight Average MW of C$_{20}^+$ product
MWD - Molecular Weight Distribution, M$_w$/M$_n$.

b) Slurry Batch Process

Oligomerization reactions were carried out by feeding about 480 ml of isobutene (dried over copper chromite, alumina and 4A molecular sieves) at 120 ml per hour to a 600 ml Parr reactor containg 2 g of the SiO$_2$-AlCl$_2$ (Catalyst II) and 0.2 ml of t-butyl chloride (1.8 mmol) as cationic initiator. The catalyst is based on a 100-200 mesh, 150A silica containing 0.9 mmol of AlCl$_2$ per gram of catalyst. The mixture was stirred overnight at the desired temperature and the product was pushed out of the reactor with nitrogen through a fritted dip tube. The catalyst was reused several times by repeating the isobutene feed and product withdrawal procedure daily. Products from each day were combined and vacuum distilled to remove C$_{20}$— products. Both light and C$_{20}$+ fractions were characterized by gas chromatography, gel permeation chromatography (GPC), and NMR. Reaction conditions and results are set out in Table 3 below.

TABLE 3

Batch Reactor with 2 g of Catalyst II (1.8 mmol AlCl$_2$)
and 1.8 mmol of t-BuCl

| | E | F | G# | H | I |
|---|---|---|---|---|---|
| Promoter | none | t-BuCl | t-BuCl | t-BuCl | t-BuCl |
| Feed Purification* | No | Yes | Yes | Yes | Yes |
| Temperature, °C. | 30 | 30 | 40 | 20 | 30 |
| Total Run Time, days | 3 | 3 | 10 | 4 | 12 |
| Conversion, % | 82 | >95 | 95 | 85 | 97 |
| % C$_{20}^+$ Selectivity | 74.1 | 67.6 | 55.8 | 61.8 | 60.4 |
| M$_n$* | 488 | 490 | 512 | 1124 | 480 |
| M$_w$* | 3264 | 4038 | 3217 | 10822 | 6815 |
| MWD | 8.9 | 8.2 | 8.4 | 9.6 | 14.2 |
| Cl, ppm | — | — | — | — | 14 |

*M$_n$ - Number Average MW of C$_{20}^+$ product
*M$_w$ - Weight Average MW of C$_{20}^+$ product
MWD - Molecular Weight Distribution, M$_w$/M$_n$.
*purified by DeOx, alumina and 4A molecular sieves
run terminated due to equipment failure The feed purity on catalyst productivity was found to be important. When isobutene was first treated with copper chromite, alumina and molecular sieves to remove any moisture and oxygenates present in the feed, high olefin conversion was observed (E vs. F). With purified isobutene, catalyst runs H and I gave >95% olefin conversions for days and were terminated only when a sudden decrease of isobutene conversion was observed. The sudden loss of catalyst activity was caused by feed impurities from a guard bed failure after prolonged usage. It is believed that with proper feed purification, the productivity of the catalyst can be greater than 1500 or even greater than 1700 g of product per g of catalyst.

The PIBs prepared in accordance with the present invention were different from commercially available samples (Polyscience, Inc., Warrington, Pa.) in two ways. First, the molecular weight distributions of PIB by SiO$_2$—AlCl$_2$ (G and H) are significantly greater than commercial samples as shown below in Table 4.

TABLE 4

Molecular Weight Distribution (MWD) Comparison

| | M$_n$ | M$_w$ | MWD |
|---|---|---|---|
| Commercial PIBs | | | |
| J | 500 | 1103 | 2.5 |
| K | 771 | 1945 | 2.5 |
| L | 1376 | 3347 | 2.4 |
| M | 2486 | 9224 | 3.7 |
| Present Invention PIBs | | | |
| G | 512 | 3217 | 8.4 |
| H | 1124 | 10822 | 9.6 |

Figure 2:
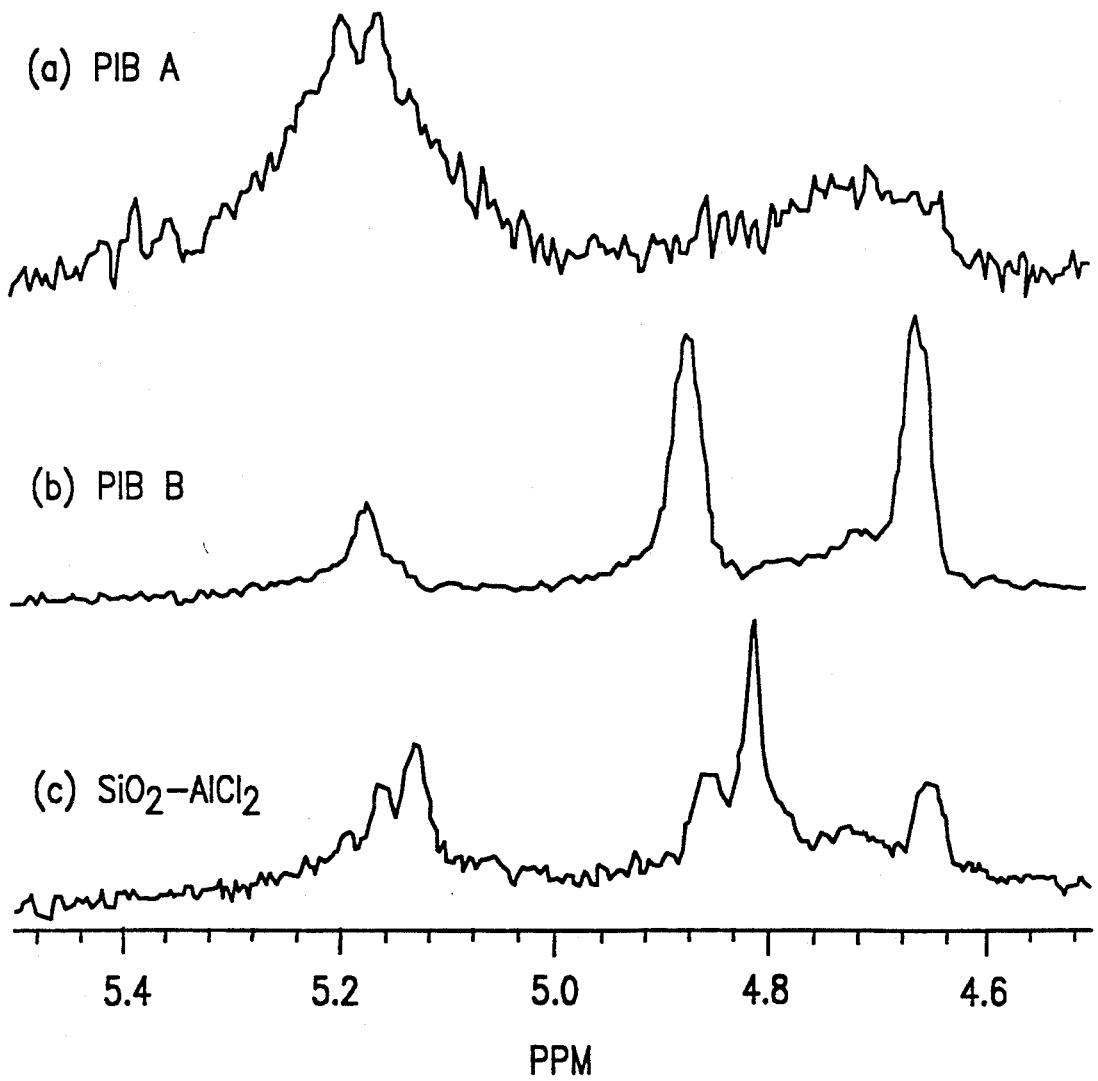
FIG. 2 is a graph comparing the H-1 NMR spectra, in the vinyl region, of two commercially available isobutylene oligomers in the vinyl region and PIBs prepared in accordance with the present invention.

Secondly, C$_{20}$+ fractions of PIBs produced over the SiO$_2$—AlCl$_2$ catalysts according to the present invention have vinylidene and tri-substituted type double bonds present in approximately equal amounts as shown by H-1 NMR as shown in Table 5 and FIG. 1 below. The lower molecular weight oligomer fractions appear to have more vinylidene than tri-substituted double bonds. Unsaturations in commercial samples range from about 80% tri-substituted double bond to about 805 vinylidene double bond as shown in FIG. 2 and Table 6 below.

TABLE 5

Relative Amount of Double Bond
in SiO$_2$—AlCl$_2$ Catalyzed Isobutene Oligomers

| | Tri-Substituted:Vinylidene | |
|---|---|---|
| | H-1 Spectra Integration | Mole Ratio |
| C$_8$ Oligomers | 1.0:7.0 | 1.0:3.5 |
| C$_{12}$—C$_{16}$ Oligomers | 1.0:2.5 | 1.0:1.2 |
| C$_{20}^+$ Oligomers | 1.0:2.2 | 1.0:1.1 |

TABLE 6

Relative Amount of Double Bond
in Polyisobutylenes

| | Tri-Substituted:Vinylidene | |
|---|---|---|
| | H-1 Spectra Integration | Mole Ratio |
| PIB A (commercial) | 1.0:0.4 | 1.0:0.20 |
| PIB by SiO$_2$—AlCl$_2$ | 1.0:2.2 | 1.0:1.1 |
| PIB B (commercial) | 1.0:7.5 | 1.0:3.8 |

It is claimed:

1. A process for the production of polyisobutylene (PIB) which comprises:
   contacting isobutene-containing feed, under heterogeneous oligomerization conditions with a catalyst composition comprising halides of a metal component anchored on a solid adsorbent inorganic oxide support by an oxygen-metal bond and a promoter selected from the group consisting of water, alkanol, alkyl halide and HCl, to provide a reaction mixture containing said polyisobutene, wherein said inorganic oxide support has a pore size of 50 to 400 angstroms;
   and separating and recovering said polyisobutene.

2. The process of claim 1 wherein said metal is a single element selected from one of Groups IIA, IIB, IIIA, IIIB, IVB, and VIB, and said adsorbent inorganic oxide is selected from group consisting of silica, silica-alumina, clay, crystalline porous silicates, silicoaluminophosphates, titania, vanadia, and rare earth oxides.

3. The process of claim 1 wherein said inorganic oxide is silica and said metal is a Group IIIA element selected from the group consisting of boron, aluminum, and gallium.

4. The process of claim 1 wherein said metal is Al and said halides are Cl−.

5. The process of claim 1 wherein said catalyst composition consists essentially of halides of a single metal component anchored on an adsorbent solid by an oxygen-metal bond and is prepared by contacting an adsorbent inorganic oxide support containing surface hydroxyl groups with organic metal halide, under conditions sufficient for said organic metal halide to react with at least a portion of said surface hydroxyl groups wherein said metal is a single element selected from one of Groups IIA, IIB, IIIA, IIIB, IVB, VB, and VIB, and said adsorbent inorganic oxide support is selected from the group consisting silica, silica-alumina, clay, crystalline porous silicates, silicoaluminophosphates, titania, vanadia, and rare earth oxides.

6. The process of claim 5 wherein said surface hydroxyl groups are silanol, said organic metal halide has the formula RMXY wherein R is alkyl or aryl, M is an element selected from Groups IIA, IIB, IIIA, IIIB, IVB, VB, and VIB of the Periodic Table, X is halogen and Y is selected from the group consisting of halogen, alkyl, alkenyl, aryl, alkoxy, and amido moities.

7. The process of claim 6 wherein said organic metal halide is $RAlCl_2$ wherein R is alkyl, and said contacting of the adsorbent inorganic oxide support containing surface hydroxyl groups with organic metal halide, is carried out in the presence of a liquid alkane.

8. The process of claim 7 wherein said inorganic oxide support is heated at temperatures ranging from 300 to 600° C. for to 8 hours, prior to said contacting of the support.

9. The process of claim 5 wherein said inorganic oxide support is a porous crystalline silicate selected from the group consisting of MCM-22 and MCM-41.

10. The process of claim 6 wherein R is alkyl, M is a Group IIIA element, and Y is selected from the group consisting of halogen and alkyl.

11. The process of claim 6 wherein RMXY is selected from the group consisting of $EtAlCl_2$, $Me_2AlCl$, $Et_2AlCl$, $Et_2AlCl/EtAlCl_2$, and $Et_2AlOMe$.

12. The process of claim 6 wherein RMXY is $EtAlCl_2$ and said adsorbent is silica.

13. The process of claim 1 wherein said oligomerization conditions comprise temperatures of −100° to 300° C. contacting times of 0.01 to 100 h, olefin conversion of at least 70 wt %, $C_{20}+$ selectivity of at least 15%, and said polyisobutylene has a halogen content of <100 ppm, weight average molecular weight ($M_w$) of 280 to 200,000, number average molecular weight ($M_n$) of 280 to 10,000, molecular weight distribution of at least 1.01, and at least 30 wt % vinylidene-type double bond content.

14. The process of claim 13 wherein said oligomerization conditions comprise temperatures of 20° to 75° C., contacting times of 0.1 to 20 h, olefin conversion of at least 80 wt %, $C_{20}+$ selectivity of at least 60%, and said polyisobutylene has a halogen content of <40 ppm, weight average molecular weight ($M_w$) of 280 to 20,000, number average molecular weight ($M_n$) of 280 to molecular weight distribution of at least 1.1, and at least 50 wt % vinylidene-type double bond content.

15. The process of claim 13 wherein said isobutene-containing feed is treated with reduced copper, alumina, and 4A molecular sieve prior to contacting with said catalyst composition.

16. The process of claim 13 wherein said oligomerization is carried out in a fixed bed reactor.

17. The process of claim 13 wherein said oligomerization is carried out in a slurry batch reactor.

18. A process for the production of polyisobutylene (PIB) which consists essentially, of:
contacting isobutene-containing feed, under heterogeneous oligomerization conditions with a catalyst composition comprising halides of a metal component anchored on a solid adsorbent inorganic oxide support by an oxygen-metal bond and a promoter selected from the group consisting of water, alkanol, alkyl halide and HCl, to provide a reaction mixture containing said polyisobutene, wherein said inorganic oxide support has a pore size of 40 to 400 angstroms;
and separating and recovering said polyisobutene by filtration.

19. The process of claim 18 wherein said metal is a single element selected from one of Groups IIA, IIB, IIIA, IIIB, IVB, VB, and VIB, said adsorbent inorganic oxide is selected from the group consisting of silica, silica-alumina, clay, crystalline porous silicates, silicoaluminophosphates, titania, vanadia, and rare earth oxides, and said promoter is tert-butyl chloride.

* * * * *

UNITED STATES PATENT AND TRADEMARK OFFICE
CERTIFICATE OF CORRECTION

PATENT NO. : 5,326,920
DATED : July 5, 1994
INVENTOR(S) : Suzzy C. Ho et al

It is certified that error appears in the above-indentified patent and that said Letters Patent is hereby corrected as shown below:

Col. 12, line 56 (claim 1), "50" should read --40--.

Col. 12, line 61 (claim 2), after "IVB" insert --VB--.

Col. 13, line 14 (claim 5), after "consisting" insert --of--.

Col. 13, line 31 (claim 8), after "for" insert --1--.

Col. 14, line 14 (claim 14), after "to" insert --2000,--.

Signed and Sealed this

Eleventh Day of October, 1994

Attest:

BRUCE LEHMAN

*Attesting Officer*          *Commissioner of Patents and Trademarks*